(12) United States Patent
Begg

(10) Patent No.: US 11,571,232 B2
(45) Date of Patent: Feb. 7, 2023

(54) CORKSCREW TISSUE RESECTING DEVICE

(71) Applicant: Covidien LP, Mansfield, MA (US)

(72) Inventor: Nikolai D. Begg, Wellesley, MA (US)

(73) Assignee: Covidien LP, Mansfield, MA (US)

( * ) Notice: Subject to any disclaimer, the term of this patent is extended or adjusted under 35 U.S.C. 154(b) by 3 days.

(21) Appl. No.: 16/851,734

(22) Filed: Apr. 17, 2020

(65) Prior Publication Data

US 2021/0322047 A1 Oct. 21, 2021

(51) Int. Cl.
*A61B 17/32* (2006.01)

(52) U.S. Cl.
CPC .......... *A61B 17/32002* (2013.01); *A61B 2017/320032* (2013.01); *A61B 2217/002* (2013.01)

(58) Field of Classification Search
CPC .. A61B 17/32002; A61B 2017/320032; A61B 2217/002; A61B 2217/005
See application file for complete search history.

(56) References Cited

U.S. PATENT DOCUMENTS

| | | | |
|---|---|---|---|
| 5,488,958 A | 2/1996 | Topel et al. | |
| 5,649,547 A | 7/1997 | Ritchart et al. | |
| 7,195,634 B2 | 3/2007 | Schmieding et al. | |
| 7,905,896 B2 * | 3/2011 | Straub | A61B 17/320783 606/170 |
| 9,078,979 B2 | 7/2015 | Fischer, Jr. | |
| 2008/0249553 A1 * | 10/2008 | Gruber | A61B 17/32002 606/171 |
| 2010/0160939 A1 | 6/2010 | Braido | |
| 2012/0197157 A1 * | 8/2012 | Ryan | A61B 10/04 600/567 |
| 2013/0046316 A1 * | 2/2013 | Sullivan | A61B 10/04 606/115 |
| 2014/0031844 A1 * | 1/2014 | Kusleika | A61B 17/320783 606/159 |
| 2014/0277036 A1 * | 9/2014 | Flynn | A61B 17/3205 606/170 |
| 2015/0223788 A1 * | 8/2015 | Walther | A61B 8/12 600/471 |
| 2018/0368872 A1 * | 12/2018 | Fukui | A61B 17/320758 |
| 2019/0343506 A1 | 11/2019 | Karapetian | |

* cited by examiner

*Primary Examiner* — Sarah A Simpson
(74) *Attorney, Agent, or Firm* — Carter, DeLuca & Farrell LLP

(57) ABSTRACT

A tissue resecting device includes a housing having an outer shaft, the outer shaft including a tool portion disposed at a distal end thereof having a window defined therein with a proximal cutting edge. An inner shaft is disposed within the outer shaft and includes proximal and distal ends, the inner shaft configured to rotate upon actuation thereof. A corkscrew member extends distally from the distal end of the inner shaft and into the window. The cork-screw member is configured to rotate concomitantly with the inner shaft and includes a barb at a distal end thereof configured to pierce and retain tissue thereon. Upon rotation of the inner shaft, the barb pierces and retains tissue and withdraws tissue proximally along the cork-screw member and into the outer shaft and wherein excess tissue is excised by the proximal cutting edge of the window as the tissue is withdrawn through the outer shaft.

18 Claims, 4 Drawing Sheets

CORKSCREW TISSUE RESECTING DEVICE

BACKGROUND

1. Technical Field

The present disclosure relates generally to the field of tissue resection. In particular, the present disclosure relates to a tissue resecting device including a cork-screw retraction mechanism for use with a cutting member.

2. Background of Related Art

Tissue resection may be performed endoscopically within an organ, such as a uterus, by inserting an endoscope (or hysteroscope) into the uterus and passing a tissue resection device through the endoscope (or hysteroscope) and into the uterus. With respect to such endoscopic tissue resection procedures, it often is desirable to distend the uterus with a fluid, for example, saline, sorbitol, or glycine. The inflow and outflow of the fluid during the procedure maintains the uterus in a distended state and flushes tissue and other debris from within the uterus to maintain a visible working space.

SUMMARY

As used herein, the term "distal" refers to the portion that is described which is farther from a user, while the term "proximal" refers to the portion that is described which is closer to a user. Further, to the extent consistent, any or all of the aspects described herein may be used in conjunction with any or all of the other aspects described herein.

Provided in accordance with an aspect of the present disclosure is a tissue resecting device which includes a housing having an elongated outer shaft extending from a distal end thereof. The elongated outer shaft includes a tool portion disposed at a distal end thereof, the tool portion including a window defined therein having a proximal cutting edge. An inner shaft is disposed within the elongated outer shaft and includes proximal and distal ends. The inner shaft is configured to rotate upon actuation thereof. A cork-screw member extends distally from the distal end of the inner shaft and into the window. The cork-screw member is configured to rotate concomitantly with the inner shaft. The cork-screw member includes a barb at a distal end thereof configured to pierce and retain tissue thereon. Upon rotation of the inner shaft, the barb pierces and retains tissue thereon and withdraws tissue proximally along the cork-screw member and into the elongated outer shaft wherein excess tissue is excised by the proximal cutting edge of the window as the tissue is withdrawn through the elongated outer shaft.

In aspects according to the present disclosure, the cork-screw member is spaced from a distal end of the window of the tool portion allowing the cork-screw member to engage tissue. In other aspects according to the present disclosure, outflow tubing is adapted to connect to a fluid management system configured to provide negative pressure to the elongated outer shaft to draw tissue into the window and through the elongated outer shaft. In yet other aspects according to the present disclosure, a motor is disposed within the housing and is configured to operably couple to the inner shaft and provide rotation thereto upon activation thereof.

Provided in accordance with an aspect of the present disclosure is a tissue resecting device which includes a housing having an elongated outer shaft extending from a distal end thereof. The elongated outer shaft includes a tool portion disposed at a distal end thereof, the tool portion including a window defined therein having a proximal cutting edge. An inner shaft is disposed within the elongated outer shaft and includes proximal and distal ends. The inner shaft is configured to move upon actuation thereof. A retention member is operably coupled to the inner shaft and extends distally into the window. The retention member is configured to move concomitantly with the inner shaft and is configured to engage tissue for withdrawal into the elongated shaft. Upon movement of the inner shaft, the retention member engages and withdraws tissue proximally into the elongated outer shaft wherein excess tissue is excised by the proximal cutting edge of the window as the tissue is withdrawn through the elongated outer shaft.

In aspects according to the present disclosure, the retention member includes a barb spaced from a distal end of the window of the tool portion allowing the retention member to engage tissue. In other aspects according to the present disclosure, outflow tubing is adapted to connect to a fluid management system configured to provide negative pressure to the outer shaft to draw tissue into the window and through the elongated outer shaft. In other aspects according to the present disclosure, a motor is disposed within the housing and is configured to operably couple to the inner shaft and provide movement thereto upon activation thereof.

In aspects according to the present disclosure, a motor is disposed within the housing and is configured to operably couple to the inner shaft and provide rotation thereto upon activation thereof, wherein rotation of the inner shaft correspondingly rotates the retention member to engage and retain tissue for withdrawal.

BRIEF DESCRIPTION OF THE DRAWINGS

Various aspects and features of the present disclosure are described hereinbelow with reference to the drawings wherein like numerals designate identical or corresponding elements in each of the several views and.

DETAILED DESCRIPTION

Figure 1:
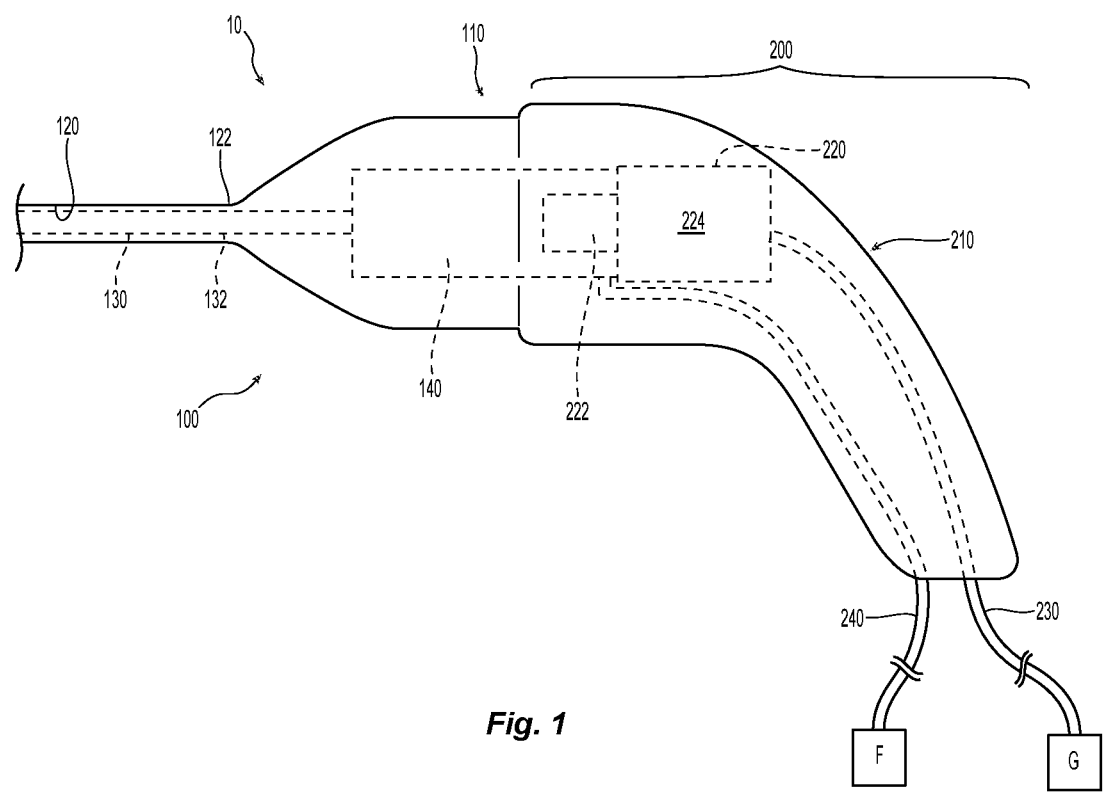
FIG. 1 is a partial side view of a proximal portion of a tissue resecting device in accordance with an aspect of the present disclosure.
Figure 2:
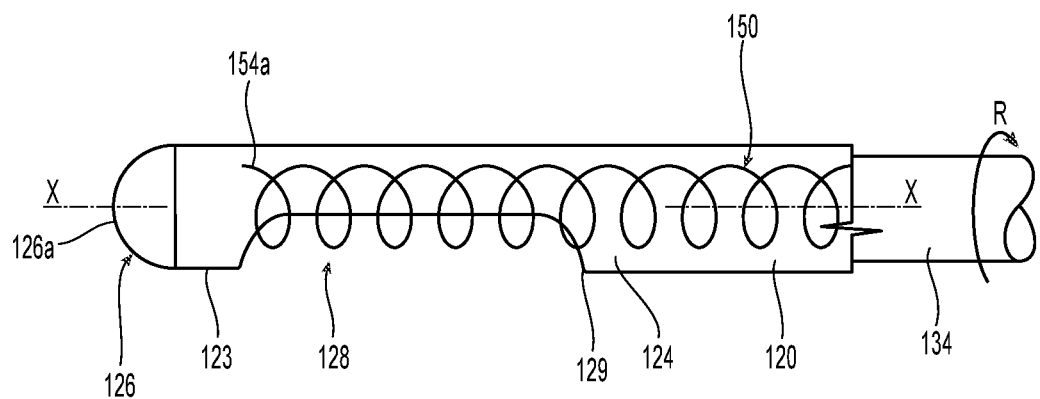
FIG. 2 is a partial side view of a distal portion of an end effector assembly of the tissue resecting device of FIG. 1.

Referring generally to FIGS. 1 and 2, a tissue resecting device 10 provided in accordance with the present disclosure and configured to resect tissue includes an end effector assembly 100 and a handpiece assembly 200. Tissue resecting device 10 is adapted to connect to a control unit "G", e.g., via cable 230, to provide power and control functionality to tissue resecting device 10, although tissue resecting device 10 may alternatively or additionally include controls associated with handpiece assembly 200 and/or a power source, e.g., battery, disposed within handpiece assembly 200. In other embodiments, tissue resecting device 10 is manually powered and/or controlled.

Tissue resecting device 10 is further adapted to connect to a fluid management system "F", e.g., via outflow tubing 240, for removing fluid, tissue, and debris from a surgical site via tissue resecting device 10. The control unit and fluid management system "F" may be integral with one another, coupled to one another, or separate from one another. The fluid management system "F" may provide negative suction to facilitate tissue resection.

With continued reference to FIGS. 1 and 2, tissue resecting device 10 may be configured as a single-use device that is discarded after use or sent to a manufacturer for reprocessing, a reusable device capable of being cleaned and/or sterilized for repeated use by the end-user, or a partially-single-use, partially-reusable device. With respect to partially-single-use, partially-reusable configurations, handpiece assembly 200 may be configured as a cleanable/sterilizable, reusable component, while end effector assembly 100 is configured as a single-use, disposable/reprocessable component. In either of the above configurations, end effector assembly 100 is configured to releasably engage handpiece assembly 200 to facilitate disposal/reprocessing of any single-use components and cleaning and/or sterilization of any reusable components. Further, enabling releasable engagement of end effector assembly 100 with handpiece assembly 200 allows for use of different end effector assemblies with handpiece assembly 200.

Figure 4:
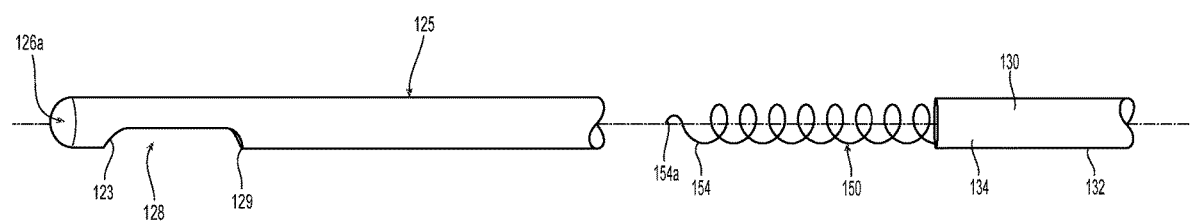
FIG. 4 is an exploded perspective view of the distal portion of the end effector assembly of FIG. 2, with parts separated.

End effector assembly 100 includes a proximal hub housing 110, an elongated outer shaft 120 fixedly engaged with and extending distally from proximal hub housing 110, an inner shaft 130 movably disposed within elongated outer shaft 120, an inner drive core 140, and a cutting member 150 (FIG. 4). Inner drive core 140 is operably disposed within proximal hub housing 110 and coupled to inner shaft 130 such that rotational input imparted to inner drive core 140, e.g., via handpiece assembly 200, drives rotation of inner shaft 130 within and relative to elongated outer shaft 120. In embodiments, inner shaft 130 may be configured to additionally or alternatively reciprocate relative to elongated outer shaft 120.

Proximal hub housing 110 of end effector assembly 100 is configured to releasably engage handle housing 210 of handpiece assembly 200, e.g., via snap-fit, threaded, luer-lock, lock-button, or other suitable engagement, and may be configured for fixed engagement with handle housing 210 or rotational engagement therewith.

Referring back to FIG. 1, handpiece assembly 200 generally includes a handle housing 210, a drive assembly 220 disposed within handle housing 210, cable 230, and outflow tubing 240. Handle housing 210 is configured to releasably engage proximal hub housing 110 of end effector assembly 100, and defines a pistol-grip configuration, although other configurations are also contemplated, e.g., a pencil-grip configuration. Handpiece assembly 200 may further include one or more controls (not shown) disposed on or operably associated with handle housing 210 to facilitate activation of drive assembly 220.

Drive assembly 220 includes a distal drive rotor 222 and a motor 224 that drives rotation of distal drive rotor 222. Distal drive rotor 222 is configured to mate with inner drive core 140 of end effector assembly 100 upon engagement of end effector assembly 100 with handpiece assembly 200 to thereby engage distal drive rotor 222 and inner drive core 140 with one another. Cable 230 provides power and/or control signals to motor 224 to control rotation of distal drive rotor 222.

Outflow tubing 240 is configured such that, with end effector assembly 100 engaged with handle housing 210, outflow tubing 240 communicates with the internal lumen of inner shaft 130 of end effector assembly 100 to receive resected tissue as well as fluid and other debris withdrawn from an internal surgical site during use. Outflow tubing 240 is configured to ultimately connect to a collection canister (not shown) or other suitable collection reservoir for collecting the tissue, fluid, and debris withdrawn from the internal surgical site.

Outflow tubing 240 may additionally or alternatively couple to a suction source (not shown) for establishing suction or negative pressure through outflow tubing 240 and the with the internal lumen of inner shaft 130 to facilitate drawing tissue, fluid, and debris into and through inner shaft 130.

Inner drive core 140 extends proximally from proximal hub housing 110 of end effector assembly 100 and is configured to engage distal drive rotor 222 of a drive assembly 220. At least a portion of distal drive rotor 222 defines a non-circular cross-section that is complementary to that of the lumen of inner drive core 140 such that engagement of distal drive rotor 222 with inner drive core 140 rotationally fixes distal drive rotor 222 with inner drive core 140. In addition, inner drive core 140 extends distally through proximal hub housing 110 and is (directly or indirectly) fixedly engaged with proximal end portion 132 of inner shaft 130 within proximal hub housing 110. Under such a configuration, rotation of inner drive core 140 imparts rotation to inner shaft 130. Thus, with end effector assembly 100 engaged with handpiece assembly 200, motor 224 may be activated to drive rotation of distal drive rotor 222, thereby driving rotation of inner shaft 130 relative to elongated outer shaft 120.

In order to engage end effector assembly 100 with handpiece assembly 200, end effector assembly 100, led by inner drive core 140, is inserted into handle housing 210 of handpiece assembly 200. Upon further insertion of end effector assembly 100 into handpiece assembly 200, inner drive core 140 is slid about distal drive rotor 222 to thereby rotatably engage distal drive rotor 222 and inner drive core 140 with one another.

Once tissue resecting device 10 is assembled, e.g., once end effector assembly 100 is engaged with handpiece assembly 200 as detailed above, tissue resecting device 10 is ready for use. In use, tissue resecting device 10 is positioned within an internal body cavity or organ, e.g., a uterus, such that the distal end portion of end effector assembly 100 is positioned adjacent tissue to be removed. Tissue resecting device 10 may be inserted through an endoscope, e.g., a hysteroscope, or other device, or may be used independently.

Once tissue resecting device 10 is positioned adjacent tissue to be removed, tissue resecting device 10 is activated. Activation of tissue resecting device 10 drives motor 224 which rotationally drives drive rotor 222. Rotation of drive rotor 222, in turn, drives rotation of inner shaft 130 relative to elongated outer shaft 120. Activation of tissue resecting device 10 also serves to activate suction through outflow tubing 240 (in embodiments where provided), thereby applying suction through inner shaft 130. With such suction applied, tissue is drawn through window 128 of elongated outer shaft 120. The suction also draws fluid and debris through inner shaft 130. The tissue, fluid, and debris suctioned through inner shaft 130 travel proximally through inner shaft 130, inflow tubing 240, and ultimately, are deposited in a collection canister (not shown).

With reference now to FIGS. 1 and 2, elongated outer shaft 120 of end effector assembly 100 includes a proximal end portion 122 extending into and fixedly engaged within proximal hub housing 110, and a distal end portion 124 including a tool portion 125. Elongated outer shaft 120 may be formed as a single construct. For example, elongated outer shaft 120 may be monolithically formed. Tool portion 125 includes a closed distal end 126 having a tip 126a and defines a window 128 proximally-spaced from closed distal end 126. Tip 126a is atraumatic for engaging tissue and manipulating tissue "T".

Tool portion 125 of elongated outer shaft 120 may be made from a substantially rigid material to promote engagement with tissue. In other embodiments, tool portion 125 may be made from a super-elastic, deformable or articulatable material to allow selective articulation of the tool member 125 via known articulation mechanisms, e.g., articulation cables (not shown), nested segments articulatable via gear arrangements or cable arrangements (not shown), shaper memory alloy mechanisms (not shown), etc.

With reference to FIG. 2, inner shaft 130 includes a proximal end portion 132 (FIG. 1) and a distal end portion 134 coupled to cutting member 150 for concomitant rotation therewith. Cutting member 150 may be detachably coupled to distal end portion 134, e.g., via snap-fit, threaded, luer-lock, lock-button, or other suitable engagement, and may be configured for fixed engagement with inner shaft 130. However, it is also contemplated that cutting member 150 may be monolithically formed with or otherwise permanently connected to inner shaft 130.

Cutting member 150 includes an elongated, cork-screw-like member 152 attached to a distal end 134 of the inner shaft 130 and extending distally therefrom. More particularly, cork-screw member 152 includes a plurality of spirals 151 extending from inner shaft 130 and terminating with a barb 154a at a distal end thereof. Barb 154a is configured to pierce tissue "T" and then retain tissue "T" for removal. Various types of barbs 154a or other types of retention mechanisms may be utilized for piecing and retaining tissue "T" for withdrawal.

Figure 3A:
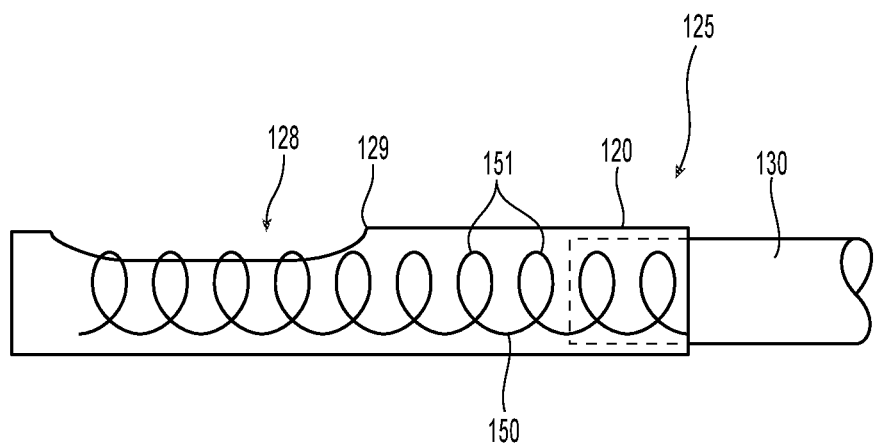
FIG. 3A is a partially enlarged, side view of a distal end portion of the end effector assembly of FIG. 2 shown prior to engaging tissue.
Figure 3B:
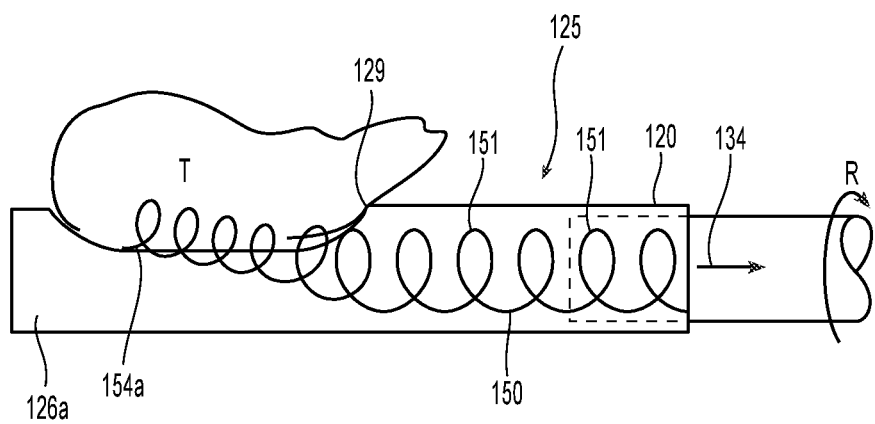
FIG. 3B is a partially enlarged, side view of a distal end portion of the end effector assembly of FIG. 2, shown drawing tissue.

FIGS. 3A and 3B show the tool portion 125 in use. More particularly, FIG. 3A shows the tool portion prior to tissue "T" engagement with the cork-screw member 152 disposed within window 128 with barb 154a poised for tissue engagement. Upon rotation of inner shaft 130, cork-screw member 152 rotates concomitantly therewith such that barb 154a engages tissue "T" by first piercing the tissue and then, as the barb is completely inserted, retaining tissue for tissue withdrawal along the cork-scree 152.

FIG. 3B shows the tissue "T" being withdrawn into window and proximally into shaft 120. As tissue "T" is being withdrawn by cork-screw 152 (i.e., tissue is pulled proximally along the spirals 151 of the cork-screw member 152), the tissue "T" is forced against a cutting edge 129 disposed on the proximal end of window 128. Excess tissue "T" is excised from the tissue body by the cutting edge 129 such that the remaining tissue body can be fully withdrawn and retained within the shaft 120. The fluid management system "F" may provide suction to the tool member 125 to facilitate the withdrawal of tissue "T" into the window 128 and through the elongated shaft 120.

Once the tissue resecting device 10 is externalized or the inner shaft 130 is externalized, rotating the inner shaft 130 in the opposite direction pushes the tissue "T" distally along the cork-screw 152 to release the retained tissue "T".

FIG. 4 shows an exploded view of the tissue resecting device 10 illustrating the various components therein.

As an alternative to handpiece assembly 200 configured for manual grasping and manipulation during use, tissue resecting devices 10 may alternatively be configured for use with a robotic surgical system wherein the end effector assembly 100 is configured to engage a robotic arm of the robotic surgical system in a similar manner as detailed above with respect to engagement of end effector assembly 100 with handpiece assembly 200. The robotic surgical system may employ various robotic elements to assist the surgeon and allow remote operation (or partial remote operation). More specifically, various robotic arms, gears, cams, pulleys, electric and mechanical motors, etc. may be employed for this purpose and may be designed with the robotic surgical system to assist the surgeon during the course of an operation or treatment. The robotic surgical system may include remotely steerable systems, automatically flexible surgical systems, remotely flexible surgical systems, remotely articulating surgical systems, wireless surgical systems, modular or selectively configurable remotely operated surgical systems, etc.

The robotic surgical system may be employed with one or more consoles that are next to the operating theater or located in a remote location. In this instance, one team of surgeons or nurses may prep the patient for surgery and configure the robotic surgical system with the surgical device disclosed herein while another surgeon (or group of surgeons) remotely control the surgical device via the robotic surgical system. As can be appreciated, a highly skilled surgeon may perform multiple operations in multiple locations without leaving his/her remote console which can be both economically advantageous and a benefit to the patient or a series of patients.

The robotic arms of the robotic surgical system are typically coupled to a pair of master handles by a controller. The handles can be moved by the surgeon to produce a corresponding movement of the working ends of any type of surgical instrument (e.g., end effectors, graspers, knifes, scissors, cameras, fluid delivery devices, etc.) which may complement the use of the tissue resecting devices described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A tissue resecting device, comprising:
   a housing including an elongated outer shaft extending from a distal end of the housing, the elongated outer shaft including a tool portion disposed at a distal end of the elongated outer shaft, the tool portion including a closed distal end and defining a window in the tool portion that is proximally spaced from the closed distal end, the window having a proximal cutting edge;

an inner shaft disposed within the elongated outer shaft and including proximal and distal ends, the inner shaft configured to rotate upon actuation of the inner shaft; and a cork-screw member extending distally from the distal end of the inner shaft and into the window, the cork-screw member configured to rotate concomitantly with the inner shaft, the cork-screw member including a plurality of spirals extending around a hollow center, and a barb at a distal end of the cork-screw member, wherein upon rotation of the inner shaft in a first direction, the barb is configured to pierce tissue and withdraw the tissue proximally along the plurality of spirals, into the hollow center, and into the elongated outer shaft to retain the tissue on the cork-screw member within the elongated outer shaft, and wherein the proximal cutting edge of the window is configured to excise excess tissue as the tissue is withdrawn onto the cork-screw member and into the elongated outer shaft, and wherein upon rotation of the inner shaft in a second direction opposite the first direction, the cork-screw member is configured to push the tissue retained on the plurality of spirals distally along the cork-screw member to release the tissue.

2. The tissue resecting device according to claim 1, wherein the cork-screw member is spaced from a distal end of the window of the tool portion allowing the cork-screw member to engage tissue.

3. The tissue resecting device according to claim 1, further comprising outflow tubing adapted to connect to a fluid management system configured to provide negative pressure to the elongated outer shaft to draw tissue into the window and through the elongated outer shaft.

4. The tissue resecting device according to claim 1, further comprising a motor disposed within the housing and configured to operably couple to the inner shaft and provide rotation to the inner shaft upon activation of the motor.

5. The tissue resecting device according to claim 1, wherein the inner shaft and the cork-screw member extend along a longitudinal axis, the cork-screw member deflectable relative to the longitudinal axis when engaged with tissue.

6. The tissue resecting device according to claim 5, wherein the elongated outer shaft extends along the longitudinal axis and the cork-screw member is deflectable relative to the elongated outer shaft.

7. The tissue resecting device according to claim 1, wherein the plurality of spirals of the cork-screw member has a non-cutting outer surface that is configured to retain tissue on the plurality of spirals.

8. The tissue resecting device according to claim 1, further comprising a handpiece assembly, and the housing is releasably engaged with the handpiece assembly.

9. A tissue resecting device, comprising:

a housing including an elongated outer shaft extending from a distal end of the housing, the elongated outer shaft including a tool portion disposed at a distal end of the elongated outer shaft, the tool portion including a closed distal end and defining a window in the tool portion that is proximally spaced from the closed distal end, the window having a proximal cutting edge;

an inner shaft disposed within the elongated outer shaft and including proximal and distal ends, the inner shaft configured to move upon actuation of the inner shaft; and a retention member operably coupled to the inner shaft and extending distally into the window, the retention member including a retention shaft disposed in a helical configuration around a hollow center, the retention member having a sharp distal tip, the retention member configured to move concomitantly with the inner shaft, wherein upon movement of the inner shaft in a first direction, the sharp distal tip of the retention member is configured to engage and withdraw tissue proximally onto the retention shaft and into the elongated outer shaft to retain the tissue on the retention member within the elongated outer shaft, and wherein the proximal cutting edge of the window is configured to excise excess tissue as the tissue is withdrawn onto the retention member and into the elongated outer shaft, and wherein upon movement of the inner shaft in a second direction opposite the first direction, the retention member is configured to push the tissue retained on the retention shaft distally along the retention member to release the tissue.

10. The tissue resecting device according to claim 9, wherein the retention member includes a barb defining the sharp distal tip, the barb spaced from a distal end of the window of the tool portion allowing the retention member to engage tissue.

11. The tissue resecting device according to claim 10, wherein the barb is disposed at a distal end of the retention shaft.

12. The tissue resecting device according to claim 9, further comprising outflow tubing adapted to connect to a fluid management system configured to provide negative pressure to the elongated outer shaft to draw tissue into the window and through the elongated outer shaft.

13. The tissue resecting device according to claim 9, further comprising a motor disposed within the housing and configured to operably couple to the inner shaft and provide movement to the inner shaft upon activation of the motor.

14. The tissue resecting device according to claim 9, further comprising a motor disposed within the housing and configured to operably couple to the inner shaft and provide rotation to the inner shaft upon activation of the motor, wherein rotation of the inner shaft correspondingly rotates the retention member to engage and retain tissue for withdrawal.

15. The tissue resecting device according to claim 9, wherein the retention member is coupled to the distal end of the inner shaft.

16. The tissue resecting device according to claim 9, wherein the inner shaft and the retention member extend along a longitudinal axis, the retention member deflectable relative to the longitudinal axis when engaged with tissue.

17. The tissue resecting device according to claim 16, wherein the elongated outer shaft extends along the longitudinal axis and the retention member is deflectable relative to the elongated outer shaft.

18. The tissue resecting device according to claim 9, wherein the retention shaft of the retention member has a non-cutting outer surface that is configured to retain tissue on the retention shaft.

* * * * *